United States Patent [19]

Naperkowski et al.

[11] Patent Number: 5,949,958
[45] Date of Patent: Sep. 7, 1999

[54] INTEGRAL FLASH STEAM GENERATOR

[75] Inventors: Susan Mary Naperkowski, Erie; Kenneth John Klobusnik; Francis John Zelina, both of Lake City, all of Pa.

[73] Assignee: Steris Corporation, Mentor, Ohio

[21] Appl. No.: 08/833,246

[22] Filed: Apr. 4, 1997

Related U.S. Application Data

[63] Continuation-in-part of application No. 08/485,736, Jun. 7, 1995.

[51] Int. Cl.[6] .............................. A01M 16/00; F24H 1/10
[52] U.S. Cl. ............................................ 392/399; 392/484
[58] Field of Search ........................... 219/272; 392/399, 392/386, 387, 394, 396, 397, 398, 484

[56] References Cited

U.S. PATENT DOCUMENTS

| | | | |
|---|---|---|---|
| 2,097,582 | 11/1937 | Beyrodt . | |
| 3,119,004 | 1/1964 | Hoop . | |
| 3,718,805 | 2/1973 | Posey | 392/397 |
| 3,980,131 | 9/1976 | Perle et al. | 122/32 |
| 4,219,725 | 8/1980 | Groninger | 219/272 |
| 4,408,116 | 10/1983 | Turner | 219/273 |
| 4,414,037 | 11/1983 | Friedheim | 134/35 |
| 4,532,412 | 7/1985 | Birocchi | 219/271 |
| 4,609,811 | 9/1986 | Danner | 219/302 |
| 4,724,824 | 2/1988 | McCoy et al. | 126/348 |
| 4,836,145 | 6/1989 | Ronchi Ne'e Marchesin | 122/4 A |
| 5,271,087 | 12/1993 | Schmid | 392/485 |
| 5,417,941 | 5/1995 | McNulty | 422/307 |
| 5,537,508 | 7/1996 | Ebbing et al. | 392/402 |
| 5,549,078 | 8/1996 | Annecharico et al. | 122/132 |

FOREIGN PATENT DOCUMENTS

| | | |
|---|---|---|
| 0 597 748 A1 | 10/1993 | European Pat. Off. . |
| 2.123.983 | 6/1971 | France . |
| 2 260 749 | 2/1974 | France . |
| 1 146 602 | 9/1960 | Germany . |
| WO 96/41099 | 12/1996 | WIPO . |

*Primary Examiner*—Teresa Walberg
*Assistant Examiner*—Daniel Robinson
*Attorney, Agent, or Firm*—Fay, Sharpe, Beall, Fagan, Minnich & McKee

[57] ABSTRACT

The present invention is a flash steam generator (10) to be used as an integral component of a steam sterilizer (30). The generator comprises a metal block (11) having a first bore (12) drilled lengthwise through the metal block (11). Surrounding the first bore (12) are a plurality of additional heater bores (14) in which heating elements (15) are inserted. The generator is integral to the sterilizer piping (31, 34) and control systems. In a preferred form, the first bore (12) provides a non-linear flow path. For example, a packing material such as monel wool (41) or a spiral dowel (45) can provide such a tortuous flow path. Alternatively, the block (11) may be provided with a plurality of fluid containing bores (51, 57, 67, 73, 81) interconnected by manifolds (59, 69, 75, 83).

17 Claims, 5 Drawing Sheets

INTEGRAL FLASH STEAM GENERATOR

This application is a continuation-in-part of U.S. Ser. No. 08/485,736, filed Jun. 7, 1995.

BACKGROUND OF THE INVENTION

This invention relates to a steam generator for use in conjunction with a device, such as a medical device steam sterilizer, that requires a supply of pressurized steam. The generator and the device are integrated into a single unit so that the generator supplies steam directly to the portion of the device requiring the steam. When integrated with a steam sterilizer the generator supplies steam directly to the sterilizer jacket or chamber.

Certain types of devices, such as steam sterilizers, require pressurized steam for their operation. Some of these devices create steam by boiling water inside a chamber within the device, such as a sterilizer chamber, using an immersion heater. An immersion heater essentially is a large heating element usually located over the bottom surface of the chamber. An immersion heater has several disadvantages, however.

An immersion heater can be a relatively large piece of equipment. It works best when its wattage can be spread out over a large heating element surface area. This keeps the watt density low and extends the life of the heating element. This large heating element surface area, however, requires a lot of space and greatly increases the size of the steam generator and of the overall device when the generator is within the device.

An immersion heater also must have its heating element completed immersed in water. To remain immersed the large heating element thus requires a large volume of water—a much larger volume of water than the sterilizer needs to complete a sterilization cycle. This large volume of water must be disposed of at the end of each pressure pulse during a sterilization cycle, including at the end of the entire sterilization cycle. Unified plumbing codes require that the water be cooled in a heat exchanger or mixed with cooling water before disposing it down a building drain. Also, a large volume of heated water requires a proportionately large amount of cooling water. Thus, the disposal process consumes a substantial amount of water. Furthermore, due to the significant amount of chamber water required, an immersion heater used with a sterilizer increases the total length of the sterilization cycle because of the time required at the start of the cycle to bring the large volume of sterilizer chamber water up to boiling temperature to start generating steam, and makes a cycle with vacuum pulses prohibitive.

An immersion heater also is prone to several service and reliability problems. The heater is prone to leaks where the heating element passes through the wall of the sterilizer chamber. The overtemperature protection device for the heater also must be inside the chamber, immersed in water or steam, and, therefore, its connections also must pass through the chamber wall creating additional potential leakage points. In addition, scale or mineral deposits build up on the heating element surface, reducing the heat transfer efficiency and heater life.

In contrast to using an immersion heater within a device, steam may be provided from a stand-alone boiler to the device requiring pressurized steam, such as a steam sterilizer. A stand-alone boiler is more costly than an immersion heater built into a device because it must be purchased as an entirely separate component from the device. In addition, a stand-alone boiler generally uses an immersion heater to produce steam, and therefore is prone to the same problems associated with that type of heater. In particular, the stand-alone boiler also requires time-consuming flushing procedures to clear mineral deposits that build up inside the boiler chamber.

The present invention provides a flash steam generator that is integral with a medical device steam sterilizer or other device requiring pressurized steam. Thus, it is less costly than a stand-alone boiler. In addition, in contrast to current steam sterilizers and stand-alone boilers, the steam generator of the present invention does not use an immersion heater to produce steam. The heating mechanism used in the present invention requires substantially less water to generate steam, and provides easier and more efficient water disposal. Furthermore, unlike an immersion heater, the heating mechanism of the present invention is not prone to leaks or the build up of scale or mineral deposits.

SUMMARY OF THE INVENTION

The present invention is a flash steam generator to be used as an integral component of a steam sterilizer or other device requiring a supply of pressurized steam. The generator comprises a metal block having a first bore drilled lengthwise, preferably through the center. Surrounding the first bore are additional lengthwise bores in which heating elements are inserted. The generator is integral to the sterilizer piping and control systems. Water is supplied to the first fluid containing bore from the sterilizer piping system, and electricity is supplied to the heating elements by the sterilizer power supply. The heating elements convert the electricity to heat, which transfers via the metal block to the first bore where the heat rapidly vaporizes the contained water in what is essentially a flash vaporization process. An overtemperature device protects the system should the heating elements or control malfunction. A safety valve exists between the block and the sterilizer chamber to protect the block and the chamber from overpressure conditions. The block and connected piping are properly insulated to prevent heat loss to the atmosphere and accidental injury to the sterilizer service person or operator.

In a preferred embodiment of the invention, the first bore is constructed to provide a tortuous path for the water/steam passing therethrough. For example, the bore can be constructed of a helical shape. Alternatively, the bore itself can be straight and a spiral dowel disposed therein. Similarly, the fluid containing bore can be packed with a fibrous material such a monel wool or alumina or with beads of metal or ceramic.

In a further preferred embodiment of this invention, the metal block is provided with several fluid containing lengthwise bores, i.e., additional to the first fluid containing bore. The several fluid containing bores are placed in sequential fluid communication with one another and provide a tortuous path and increased residence time for the water/steam in the generator.

DETAILED DESCRIPTION OF THE INVENTION

Figure 1:
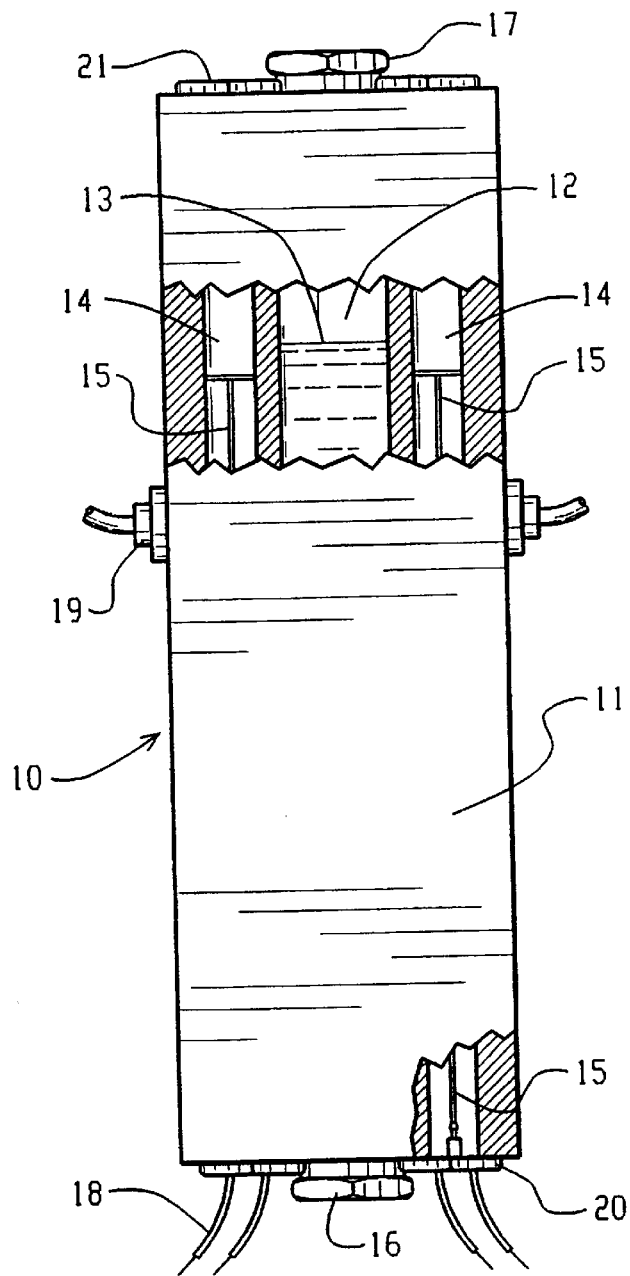
FIG. 1 is a side view of the integral flash steam generator of the present invention, with partial cut-away views showing internal features.

Referring now to reference numerals in the drawings, wherein like numerals are used to represent like elements throughout the description, a flash steam generator of the present invention is indicated generally by reference numeral 10. The generator comprises a block of metal 11, preferably carbon steel, although other heat-transferring metals may be used provided the metal exhibits sufficient strength to withstand system pressure of at least 20 psi and preferably 33 psi.

The metal block 11 may be mounted on the side of a steam sterilizer. The precise shape and dimensions may vary depending upon the sterilizer, and the block may be sized and shaped to fit any common steam sterilizer or to accommodate any common heating elements. Preferably, the metal block is elongated into a rectangular prism and mounted on the side of the sterilizer frame, although other shapes such as square blocks and cylinders may be used. Again, the shape considerations are governed primarily by the desire to manufacture a uni-body device which is suited to a high pressure environment.

A first bore 12, preferably cylindrical in shape, is drilled through the entire length of the center of the metal block 11. As further described below, the first bore provides a chamber for receiving water 13 to be converted to steam. The first bore is sized to receive a volume of water that is sufficiently small to be vaporized rapidly in what amounts to essentially a flash vaporization process.

In addition to the first bore 12 are a plurality of heater bores 14, preferably drilled lengthwise through the metal block substantially parallel to the first bore. In the preferred embodiment, each heater bore 14 has a first bore end at the bottom of the metal block and a second bore end toward the top of the metal block. The heater bores 14 should extend at least substantially the entire length of the metal block, and preferably should extend through the entire metal block to permit easier access to the heater bores for maintenance purposes.

The heater bores 14 are sized to receive a heating element 15. Electric cartridge heaters are particularly appropriate for use as the heating element in this device because they are commonly elongated and thin so that each heating element can be inserted into a heater bore and extend from the first bore end substantially to the second bore end.

Figure 2:
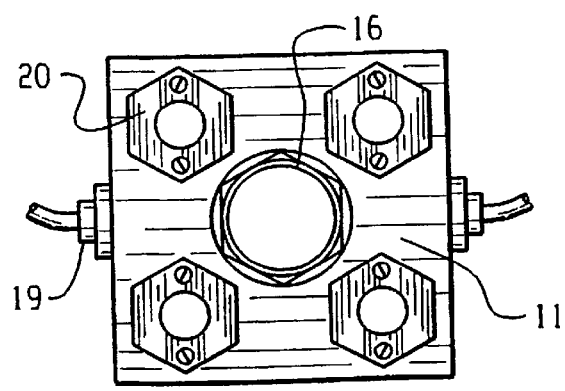
FIG. 2 is a bottom view of the generator shown in FIG. 1.

FIGS. 1 and 2 illustrate a preferred configuration of the heater bores 14, the electric cartridge heaters 15, and the first bore 12. In this preferred embodiment, the electric cartridge heaters are chosen to be thin enough so that the heater bores are narrow in comparison to the center bore. This ensures that there are a sufficient number of heating elements to create heat in an amount sufficient to vaporize the water contained in the first bore.

FIG. 2 depicts a preferred embodiment having four heater bores 14, each containing an electric cartridge heater 15, surrounding the first bore 12 located in the center of the metal block. As seen in FIG. 2, the electric cartridge heaters may be mounted within the heater bores using screw plates 20 and end plates 21, although other mechanisms to mount the heaters known in the art may be used. Note that any number and arrangement of heater bores and electric cartridge heaters may be incorporated into the metal block so long as sufficient heat can be generated by the heaters to produce steam.

The metal block 11 is fluidly connected to the sterilizer piping system 31, 34. The metal block 11 comprises a bottom end having a first female NPT thread 16 extending downward from the first bore. This thread is a standard thread that will accept typical piping used with sterilizers. The first NPT thread connects the first bore to sterilizer piping 31 from which the first bore receives its supply of water. The metal block also comprises a top end having a second female NPT thread 17 extending upward from the first bore. The second NPT thread provides a fluid connection via piping 34 between the first bore 12 and the sterilization chamber 30, thereby permitting steam to be transferred from the generator water chamber to the sterilizer chamber for use during the sterilization cycle. In addition, each of the heating elements 15 is electrically connected to the sterilizer power supply by wires 18. Thus, the sterilizer power supply provides the electricity to the heating elements, which convert the electricity to heat for producing the steam.

Figure 3:
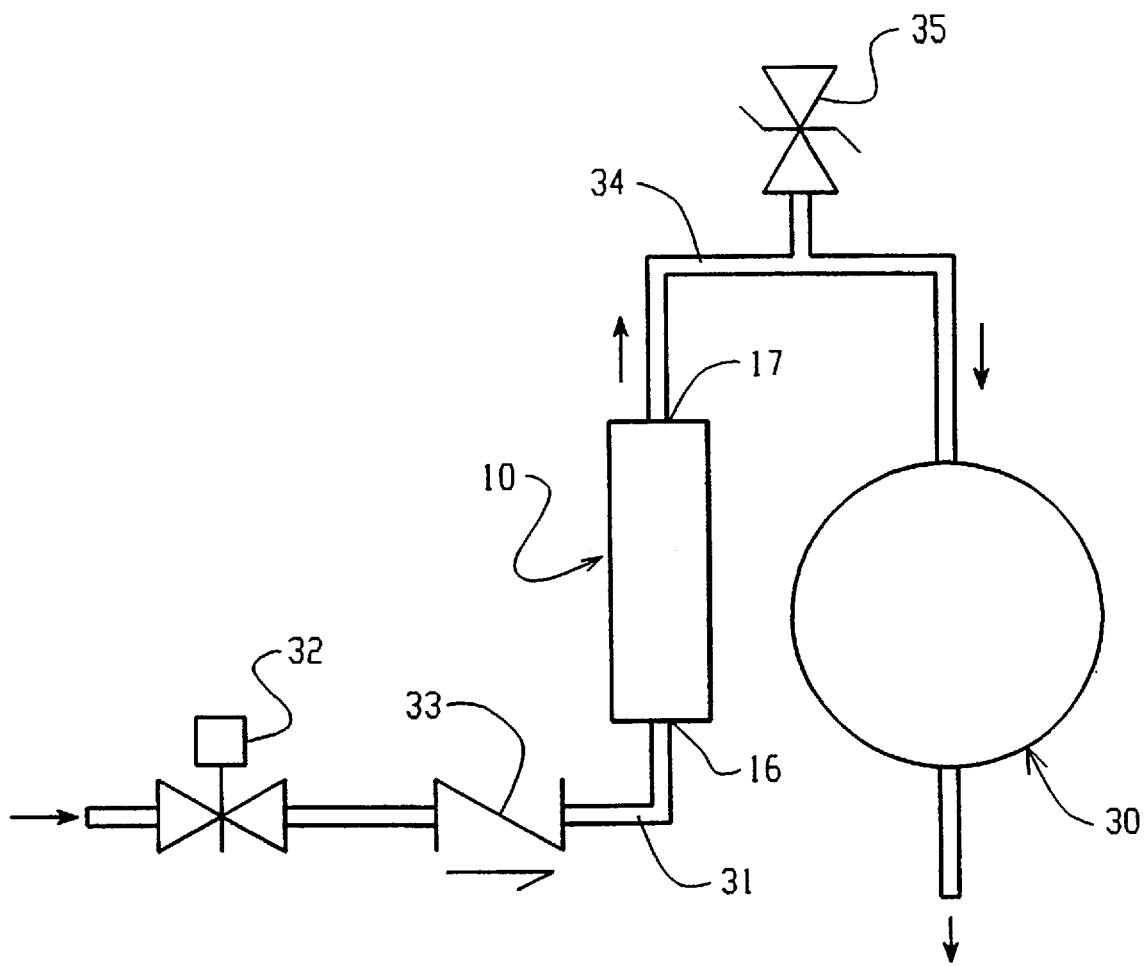
FIG. 3 is a schematic drawing of the flash steam generator of the present invention integrated into a sterilizer system.

FIG. 3 is a schematic depicting how the steam generator 10 is used integrally with a steam sterilizer 30. Water is supplied from sterilizer piping 31 through the first female NPT thread 16 to the first bore of the generator. The amount of water transferred to the generator is controlled by a solenoid valve 32 operated by the sterilizer control system, and is sufficiently small enough to be vaporized in what is essentially a flash vaporization process. Alternatively, a metering pump can be used to provide precise quantities of water to the generator. The sterilizer piping system 31 also contains a check valve 33 to prevent the backflow of water out of the steam generator. The sterilizer control system also is used to control the flow of electricity from the sterilizer power supply to the heating elements 15. When the first bore 12 is injected with water 13 and the heating elements 15 are activated, heat transfers from the heating elements, through the metal block 11 to the first bore. The heat then flash vaporizes the water 13 located in the first bore 12 to produce steam. Then an additional amount of water is injected into the first bore and vaporized in the same manner.

The process continues in this manner, producing more steam from the series of water injections. As steam is produced, the pressure inside the first bore 12 increases. The steam is forced under pressure through the second female NPT thread 17, through a fluid pathway 34 connecting the generator 10 to the sterilization chamber 30, and into the sterilization chamber. The metal block 11 and the generator-to-chamber pathway are properly insulated to prevent heat loss to the atmosphere and human injury from inadvertent contact with the generator apparatus. The device also is equipped with two other safety features. An overtemperature device 19 is mounted on the metal block 11 and shuts down the heaters in the event the heaters are energized through a control malfunction. In addition, a safety release valve 35 is provided between the metal block 11 and the sterilization chamber 30 that can release excess pressure to protect the block and the chamber from overpressure conditions.

Figure 4:
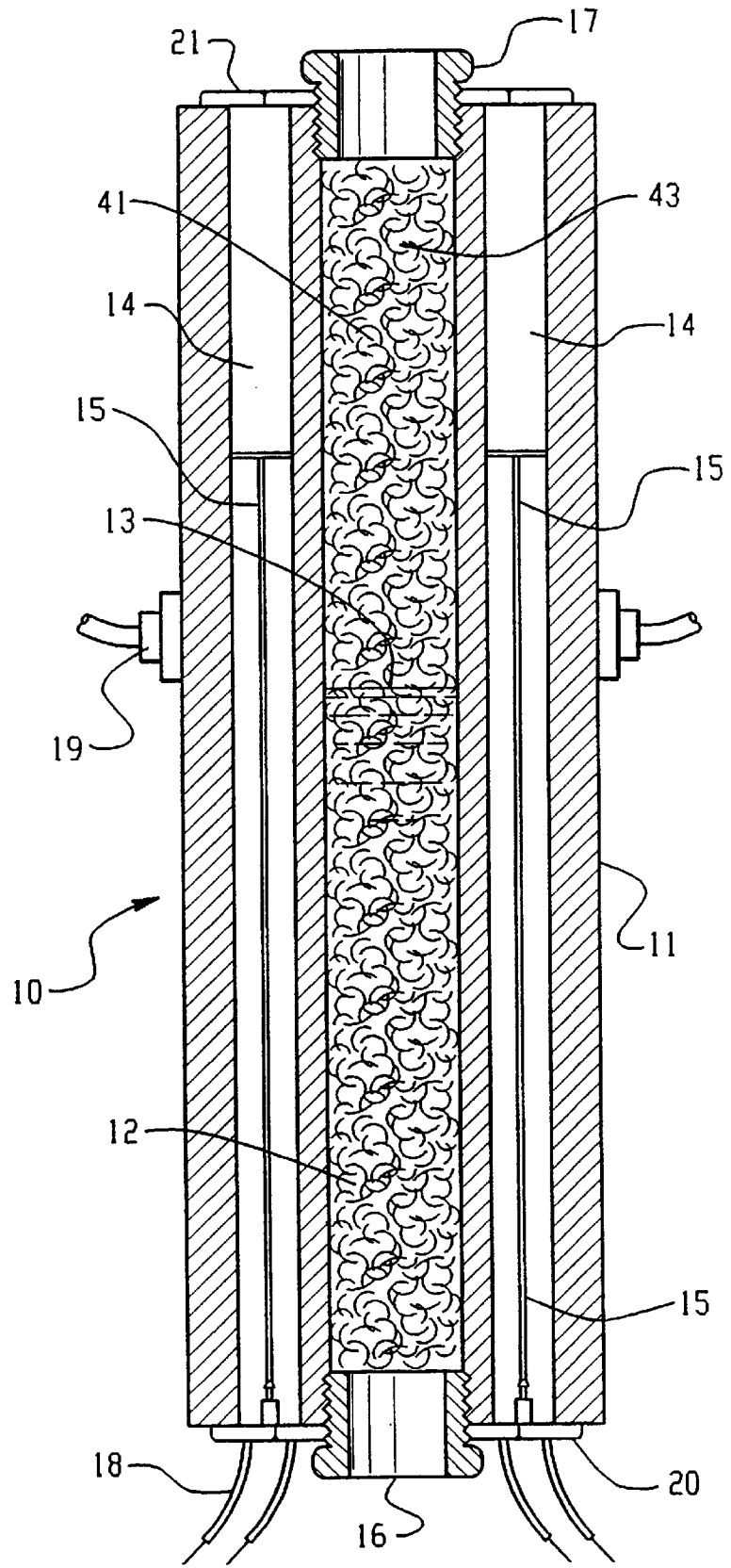
FIG. 4 is a side cross-sectional view of an alternative form of the invention wherein monel wool is disposed within a fluid containing bore.

Referring now to alternative preferred embodiments of the invention, FIG. 4 depicts the flash steam generator 10 modified to include a packing material of monel wool 41 or other fibrous material capable of withstanding high temperatures (for example, FiberFrax) within the first bore 12.

The packing material 41 provides a tortuous path for the water 13 and steam 43 which increases residence time, provides more contact area and results in a better quality of steam. In addition, the fibrous packing material retains condensate via surface tension. Accordingly, the use of the packing material 41 results in more efficient steam generation and a higher quality steam, i.e. dry steam. Obviously, other packing materials such as metal or ceramic beads, etc. can also be utilized to create a torturous path.

Figure 5:
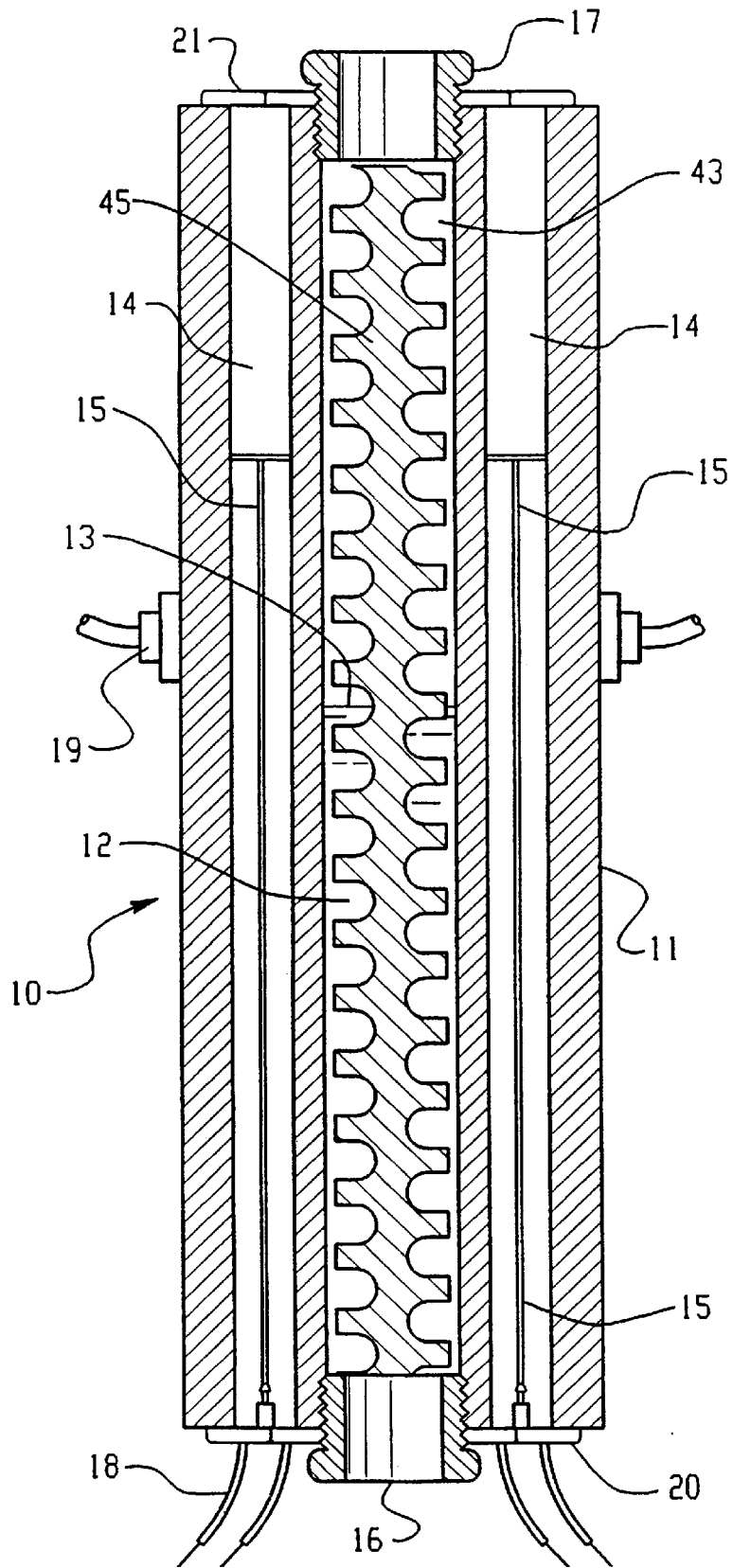
FIG. 5 is a side cross-sectional view of an alternative form of the invention wherein a spiral dowel is disposed within a fluid containing bore.
Figure 6:
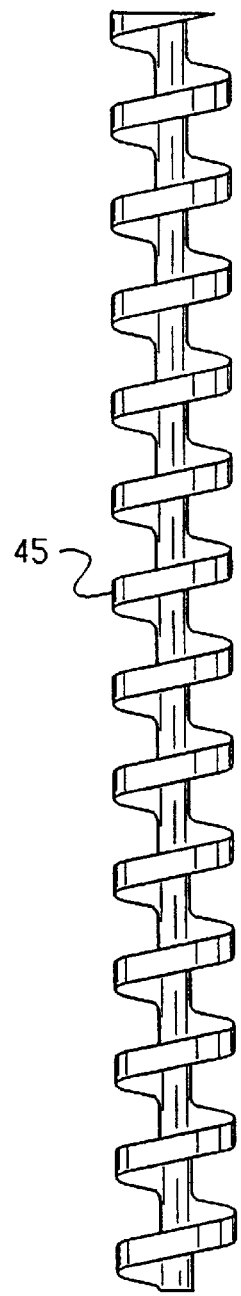
FIG. 6 is a side view of the spiral dowel of FIG. 5.

Referring now to FIGS. 5 and 6, an alternative form of the invention is depicted wherein a spiral rod 45 is inserted into the first bore 12 and functions as a packing material. As with the fibrous packing material, the spiral rod 45 creates a tortuous path for the water 13 and steam 43 as it passes upwardly through the bore 12. As with the fibrous material depicted in FIG. 4, the spiral rod 45 creates an environment in which the water 10 and steam 43 frequently contact heated surfaces within the generator device 10 occurs. This, in combination with the increased residence time, results in a more efficient and rapid generation of drier, more desirable steam. Preferably, the spiral rod 45 is comprised of a good heat conduction material such as brass, aluminum or bronze.

Figure 8:
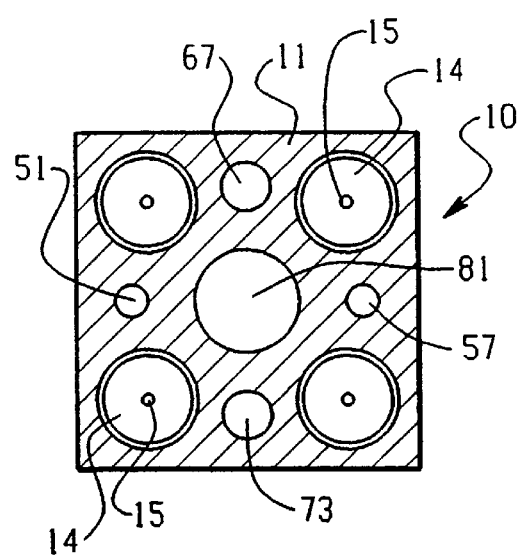
FIG. 8 is a cross section view taken along line 8—8 of FIG. 7.
Figure 7:
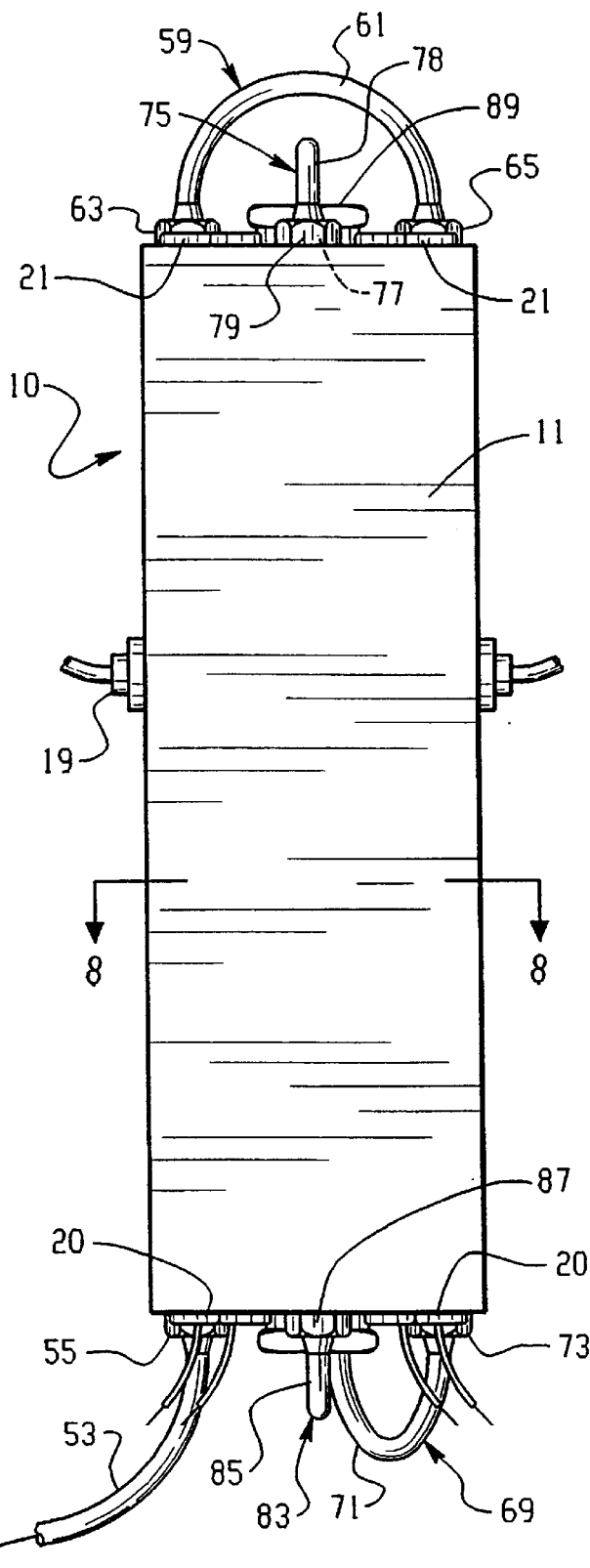
FIG. 7 is a side view of the inventive generator having several sequential fluid containing bores.

Referring now to FIGS. 7 and 8 a further preferred embodiment of the invention is depicted wherein a plurality of interconnected, generally parallel, lengthwise bores are employed to increase the residence time of the water/steam in the generator 10 and to provide increased contact with heated surfaces. In this embodiment, a first inlet bore 51 is in fluid communication with the sterilizer piping system 31 via a conduit 53 secured to the metal block 11 by an NPT threaded connector 55. Water passes through the bore 51 and begins its transformation into steam. At least partially vaporized water/steam exits the bore 51 and passes to a bore 57 via a manifold 59 having a conduit 61, a first NPT threaded connector 63 secured into the bore 51 and a second NPT threaded connector 65 secured into the bore 57. Water/steam passes through the bore 57 and is directed to a bore 67 via a manifold 69. The manifold 69 is comprised of a conduit 71, a first NPT threaded connector 73 secured into the bore 57 and a second NPT threaded connector (not shown) secured into the bore 67. Water/steam then travels through the bore 67 and is directed to a fourth bore 73 via a manifold 75. The manifold 75 is comprised of a first NPT threaded connector 77 secured into the bore 67, a conduit 78 and a second NPT threaded connector 79 secured into the bore 73. Water/steam next passes through the bore 73 and is directed into a fifth bore 81 via a manifold 83 which is comprised of a conduit 85 having a first end secured via a NPT threaded connector 87 into the bore 73 and a second end secured via a NPT threaded connector (not shown) into the bore 81. The NPT threaded connector 89 is positioned at a second end of the bore 81 and provides an excellent quality steam to the sterilizer piping system 34.

In a preferred form of this invention, each of the bores receives a coating of corrosive resistant material such as nickel, platinum, copper which can be deposited via, for example, an electrodeless sputtering procedure. In accord with this design, a significant increase in residence time is achieved for the water/steam for a given size steam generator apparatus 10. Similarly, the overall energy efficiency is improved because the mass of the apparatus is not increased while residence time is increased. In addition, the manifold system forming the interconnections between the bores provides a tortuous path for the water/steam, creating frequent contacts of the water/steam with the heated surfaces of the device. Accordingly, a more efficient generation of steam is achieved and a dryer steam is provided by the device.

As shown in this preferred embodiment, the series of parallel bores are constructed such that the first bore has the smallest diameter with each subsequent bore increasing in diameter. By this design, good steam flow is achieved as more energy is imparted to the water causing an increase in gas expansion and pressure.

Although the most readily manufacturable form of the invention is manifold system as described. It is also envisioned that the metal block could be machined to include integral passages interconnecting each of the generally parallel lengthwise bores.

From the above description the advantages of the steam generator of the present invention are clear. Immersion heaters require that the heating element remain submerged in water at all times throughout the sterilization cycle. Due to the large surface area of immersion heaters, this requires substantially more water than that used in the series of water injections in the flash vaporization process of the present invention. The present invention, therefore, reduces total water-to-steam usage, thus reducing the initial start-up time required to produce steam. In addition, only a minimal amount of hot water remains for disposal between pulses in a sterilization cycle and/or at the end of the cycle. Because the present invention only uses enough water for the steam required, less water is used resulting in a substantial conservation of water.

The integral flash steam generator provides other advantages over an immersion heater or stand-alone boiler. In contrast to these other devices, the heating elements of the integral flash generator have no element portions submerged in water or steam that provide potential points of leakage. In addition, because the water never contacts the heating elements of the present invention, the heating elements are not prone to the build-up of scale or mineral deposits as are immersion heater elements. Furthermore, the heater watt density is dispersed, e.g. divided by four in the embodiment of FIG. 8.

The flash steam generator also provides the advantage of being integral with the sterilizer or other device. The generator receives its water from the sterilizer piping and operates under electronic control of the sterilizer control system. Thus it requires no additional piping or electronics to operate, making it less expensive to manufacture and install. The steam generator may be installed on the sterilizer at the manufacturing stage, or alternatively, provided as a sterilizer accessory to be retrofitted to the sterilizer as described above.

While a certain preferred embodiment of this invention has been described, it is understood by those skilled in the art that many modifications are possible without departing from the principles of this invention as defined in the claims that follow.

We claim:

1. A flash steam generator integral with a piping system of a sterilizer comprising;

an elongated block of metal having multiple fluid containing bores extending generally lengthwise through the block, said multiple bores in serial fluid communication to provide a repeating flow path through said block and in fluid connection with the sterilizer piping system, each of said multiple bores having a progressively larger diameter in the direction of fluid flow than the preceding bore; and a plurality of heating elements in electrical connection with a power supply and in thermal connection with said fluid containing bores.

2. The flash steam generator according to claim 1 wherein the metal block comprises carbon steel.

3. The flash steam generator according to claim 1 wherein the metal block comprises an elongated one piece rectangular shaped prism.

4. The flash steam generator according to claim 1 wherein the heating elements are electric cartridge heaters.

5. The flash steam generator according to claim 1 wherein said fluid containing bore includes a coating of Ni, Cu and/or Pt.

6. The flash steam generator of claim 1 wherein said bores are substantially linear.

7. A sterilization device for the decontamination of equipment, said device including a sterilization chamber pressurizable to at least 20 psi and a steam generating apparatus, said steam generating apparatus comprised of an elongated metallic block including at least two bores containing heating elements and a first passage in which water is converted into steam, said first passage extending from a first end to a second end of said metallic block, a second passage extending from the second end of the metallic block to the first end, an arcuate connector connecting the first and second passages at the second end of the block, the second passage being larger in diameter than the first passage, and said heating elements disposed adjacent said passages.

8. The device according to claim 7 wherein the heater bores are substantially parallel to the first and second passages.

9. The flash steam generator according to claim 8 wherein the metal block includes four heater bores containing heating elements.

10. The device according to claim 7 wherein said first and second passages include a packing material.

11. The device according to claim 7 including at least four serially connected passages and at least two heating elements disposed adjacent said passages.

12. The device according to claim 7 wherein a non-linear flow path is created through the passages by a spiraled dowel.

13. The sterilization device of claim 7 wherein said metallic block is cylindrical or rectangular.

14. The sterilization device of claim 7 wherein said metallic block is comprised of metal possessing sufficient strength to withstand pressure within said bores up to 50 psi.

15. The sterilization device of claim 7 including at least four passages serially connected by arcuate conduits.

16. A process for the flash steam generation of steam to a piping system of a steam sterilizer comprising:

supplying water to a first bore in a block of metal, said bore extending through the block, providing thermal energy to said water in said bore via a plurality of heating elements in electrical connection with a power supply, said water exiting said first bore as steam, feeding the steam from the first bore to a second bore extending back through the block of metal, the second bore being larger in cross-section than the first bore, providing thermal energy to the steam and unvaporized water droplets in the second bore, feeding the steam from the second bore to a third bore extending back through the block of metal, the third bore being larger in cross-section than the second bore, providing thermal energy to the steam and any unvaporized water droplets in the third bore, supplying the steam to the sterilizer piping system.

17. A sterilization device for the decontamination of equipment, said device including a sterilization chamber pressurizable to at least 20 psi and a steam generating apparatus, said steam generating apparatus comprised of an elongated metallic block capable of withstanding at least 20 psi and including at least two bores containing heating elements and a plurality of passages through the block in which water is converted into steam, each of said passages extending between a first end and a second end of said metallic block, conduits connecting the passages in series, each of the passages having a progressively larger cross-section in a direction of fluid flow than the preceding passage.

* * * * *